United States Patent [19]

Vandenbergh et al.

[11] Patent Number: 5,665,534
[45] Date of Patent: Sep. 9, 1997

[54] METHOD OF DETECTING BOVINE DIARRHOEA VIRUS INFECTION, NUCLEOTIDE SEQUENCE ENCODING A PROTEIN INDUCED BY THIS VIRUS INFECTION AND RECOMBINANT PROTEINS AND ANTIGENS RELATING THERETO

[75] Inventors: Danielle Marie Helene Jeanne Vandenbergh, Cheratte; Corine Martine Therese Ghislaine LeComte, Ocquier, both of Belgium; Gilles-Emile Chappuis, Lyons; Jean-Jacques Pin, Saint Bonnet de Mure, both of France

[73] Assignee: Rhone Merieux, Lyons, France

[21] Appl. No.: 417,276

[22] Filed: Apr. 5, 1995

Related U.S. Application Data

[63] Continuation of Ser. No. 895,999, Jun. 11, 1992, abandoned.

[30] Foreign Application Priority Data

Jun. 11, 1991 [FR] France ................... 91 07076

[51] Int. Cl.⁶ .................. C12Q 1/70; G01N 33/53
[52] U.S. Cl. ...................................... 435/5; 435/7.1
[58] Field of Search ................ 435/5, 7.1, 7.92, 435/7.93, 69.1, 252.3

[56] References Cited

U.S. PATENT DOCUMENTS

| | | | |
|---|---|---|---|
| 4,391,904 | 7/1983 | Litman et al. | 435/7 |
| 5,008,373 | 4/1991 | Kingsman et al. | 530/350 |
| 5,206,163 | 4/1993 | Renard et al. | 435/240.2 |

FOREIGN PATENT DOCUMENTS 0 208 672  1/1987  European Pat. Off. .

OTHER PUBLICATIONS

Veterinary Microbiology, vol. 23, 1990, Amsterdam NL pp. 193–201; C. LeComte et al., 'ELISA detection of bovine viral diarrhoea virus specific antibodies. . . '.

Virology, vol. 184, No. 1, 1988, pp. 191–199; M.S. Collett "Molecular cloning and nucleotide sequence of the pestivirus bovine viral diarrhea virus".

Biochemical and Biophysical Research Communications, vol. 178 No. 3, 15 Aug. 1991, pp. 1326–1334; J. Kwang et al, "Expression of the p80 region of bovine viral diarrhea . . .".

Tiollais et al, Nature 317, 489–495 (1985) "hepatitis B Virus".

Atkinson et al, Pestic Sci 28(2):215–224 (1990) "Baculoviruses as Vectors for foreign gene expression . . . " (Biosis Abstract).

*Primary Examiner*—Eggerton A. Campbell
*Attorney, Agent, or Firm*—Larson and Taylor

[57] ABSTRACT

The invention is directed to a method of detecting infection of a blood sample by various strains of bovine diarrhoea virus (BVD) including a first test wherein anti-bovine diarrhoea virus antibodies are detected by means of a recombinant antigen comprising the BVD p80 protein expressed by a eukaryotic host and a second test wherein viral particles are detected by means of antibodies directed against the BVD p80 viral protein. The method is particularly useful in detecting pathogenic conditions such as persistent viremias and acute infections caused by BVD viruses, and is particularly advantageous because it is an extremely sensitive and efficient test and because it is capable of detecting infections caused by any one of a wide variety of BVD strains. The recombinant antigen employed in the method is preferably encoded by the nucleotide sequence listed as SEQ ID No: 1.

22 Claims, 3 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 2236 base pairs
( B ) TYPE: nucleic acid ( C ) STRANDEDNESS: double
( D ) TOPOLOGY: linear ( i i ) MOLECULE TYPE: cDNA ( v i ) ORIGINAL SOURCE:
   ( A ) ORGANISM: Bovine viral diarrhea virus
( B ) STRAIN: Osloss ( i x ) FEATURE:
( A ) NAME/KEY: CDS
( B ) LOCATION: 40..2229
( D ) OTHER INFORMATION: /product="protein P80"
/ gene= "p80"

( x i ) SEQUENCE DESCRIPTION: SEQ ID NO:1:

TCTAGAAATT TTGTTTAACT TTAAGAAGGA GATATACCC ATG GGA CTG GAA ACC 54
Met Gly Leu Glu Thr
1 5

GGA TGG GCC TAC ACA CAC CAA GGC GGC ATA AGC TCA GTA GAC CAT GTG 102
Gly Trp Ala Tyr Thr His Gln Gly Gly Ile Ser Ser Val Asp His Val
10 15 20

ACC GCA GGC AAA GAC CTA CTG GTT TGT GAT AGT ATG GGT AGG ACA AGA 150
Thr Ala Gly Lys Asp Leu Leu Val Cys Asp Ser Met Gly Arg Thr Arg
25 30 35

GTG GTT TGC CAA AGT AAC AAC AAG TTA ACT GAT GAG ACA GAA TAT GGT 198
Val Val Cys Gln Ser Asn Asn Lys Leu Thr Asp Glu Thr Glu Tyr Gly
40 45 50

GTC AAG ACG GAC TCC GGA TGT CCA GAT GGT GCC AGG TGC TAC GTA TTA 246
Val Lys Thr Asp Ser Gly Cys Pro Asp Gly Ala Arg Cys Tyr Val Leu
55 60 65

AAT CCA GAG GCA GTA AAT ATA TCA GGG TCC AAG GGA GCT GCT GTA CAC 294
Asn Pro Glu Ala Val Asn Ile Ser Gly Ser Lys Gly Ala Ala Val His
70 75 80 85

CTC CAA AAA ACA GGT GGG GAA TTC ACA TGT GTT ACT GCA TCG GGA ACT 342
Leu Gln Lys Thr Gly Gly Glu Phe Thr Cys Val Thr Ala Ser Gly Thr
90 95 100

CCA GCC TTC TTT GAC CTG AAA AAT TTG AAG GGA TGG TCA GGT CTA CCC 390
Pro Ala Phe Phe Asp Leu Lys Asn Leu Lys Gly Trp Ser Gly Leu Pro
105 110 115

ATA TTT GAG GCT TCT AGT GGC AGG GTG GTC GGC AGA GTT AAA GTA GGA 438
Ile Phe Glu Ala Ser Ser Gly Arg Val Val Gly Arg Val Lys Val Gly
120 125 130

AAG AAT GAG GAA TCC AAG CCC ACA AAA TTA ATG AGT GGT ATC CAA ACC 486
Lys Asn Glu Glu Ser Lys Pro Thr Lys Leu Met Ser Gly Ile Gln Thr
135 140 145

GTC TCA AAA AGC ACA GCC GAT TTA ACA GAG ATG GTC AAG AAG ATA ACC 534
Val Ser Lys Ser Thr Ala Asp Leu Thr Glu Met Val Lys Lys Ile Thr
150 155 160 165

AGC ATG AAC AGG GGA GAC TTT AAG CAG ATA ACC CTT GCA ACA GGG GCA 582
Ser Met Asn Arg Gly Asp Phe Lys Gln Ile Thr Leu Ala Thr Gly Ala
170 175 180

GGA AAA ACT ACA GAA CTC CCA AAG GCA GTG ATA GAG GAG ATA GGA AGA 630
Gly Lys Thr Thr Glu Leu Pro Lys Ala Val Ile Glu Glu Ile Gly Arg
185 190 195

CAC AAG CGG GTG CTA GTG CTT ATA CCA TTG AGA GCA GCA GCT GAG TCA 678
His Lys Arg Val Leu Val Leu Ile Pro Leu Arg Ala Ala Ala Glu Ser
200 205 210

GTC TAT CAA TAC ATG AGA TTG AAA CAT CCC AGT ATC TCC TTC AAC TTA 726
Val Tyr Gln Tyr Met Arg Leu Lys His Pro Ser Ile Ser Phe Asn Leu
215 220 225

AGA ATA GGG GAC ATG AAA GAA GGG GAC ATG GCA ACT GGG ATC ACC TAC 774
Arg Ile Gly Asp Met Lys Glu Gly Asp Met Ala Thr Gly Ile Thr Tyr
230 235 240 245

| | | | | | | | | | | | | | | | | |
|---|---|---|---|---|---|---|---|---|---|---|---|---|---|---|---|---|
| GCC | TCA | TAT | GGA | TAT | TTT | TGC | CAA | ATG | CCG | CAG | CCG | AAG | CTC | AGG | GCC | 822 |
| Ala | Ser | Tyr | Gly | Tyr | Phe | Cys | Gln | Met | Pro | Gln | Pro | Lys | Leu | Arg | Ala | |
| | | | 250 | | | | | 255 | | | | | | 260 | | |
| GCA | ATG | GTA | GAG | TAT | TCA | TAC | ATA | TTT | CTG | GAT | GAG | TAT | CAC | TGT | GCT | 870 |
| Ala | Met | Val | Glu | Tyr | Ser | Tyr | Ile | Phe | Leu | Asp | Glu | Tyr | His | Cys | Ala | |
| | | | 265 | | | | | 270 | | | | | 275 | | | |
| ACT | CCT | GAG | CAG | TTG | GCT | GTC | ATA | GGA | AAA | ATT | CAC | AGA | TTT | TCT | GAA | 918 |
| Thr | Pro | Glu | Gln | Leu | Ala | Val | Ile | Gly | Lys | Ile | His | Arg | Phe | Ser | Glu | |
| | | 280 | | | | | 285 | | | | | 290 | | | | |
| AGC | ATA | AGG | GTG | GTT | GCT | ATG | ACC | GCC | ACC | CCA | GCA | GGG | TCA | GTA | ACT | 966 |
| Ser | Ile | Arg | Val | Val | Ala | Met | Thr | Ala | Thr | Pro | Ala | Gly | Ser | Val | Thr | |
| | 295 | | | | | 300 | | | | | 305 | | | | | |
| ACA | ACA | GGG | CAA | AAA | CAC | CCA | ATA | GAA | GAA | TTC | ATA | GCT | CCT | GAG | GTG | 1014 |
| Thr | Thr | Gly | Gln | Lys | His | Pro | Ile | Glu | Glu | Phe | Ile | Ala | Pro | Glu | Val | |
| 310 | | | | | 315 | | | | | 320 | | | | | 325 | |
| ATG | AAA | GGG | GAA | GAC | CTT | GGA | AGC | CAG | TTC | CTT | GAC | ATA | GCG | GGG | CTA | 1062 |
| Met | Lys | Gly | Glu | Asp | Leu | Gly | Ser | Gln | Phe | Leu | Asp | Ile | Ala | Gly | Leu | |
| | | | | 330 | | | | | 335 | | | | | 340 | | |
| AAA | ATC | CCG | GTT | GAG | GAG | ATG | AAG | GGT | AAC | ATG | CTG | GTC | TTC | GTA | CCC | 1110 |
| Lys | Ile | Pro | Val | Glu | Glu | Met | Lys | Gly | Asn | Met | Leu | Val | Phe | Val | Pro | |
| | | | 345 | | | | | 350 | | | | | 355 | | | |
| ACA | AGA | AAC | ATG | GCA | GTT | GAT | GTA | GCC | AAG | AAA | CTA | AAA | GCC | AAG | GGC | 1158 |
| Thr | Arg | Asn | Met | Ala | Val | Asp | Val | Ala | Lys | Lys | Leu | Lys | Ala | Lys | Gly | |
| | | 360 | | | | | 365 | | | | | 370 | | | | |
| TAC | AAC | TCA | GGG | TAT | TAC | TAC | AGT | GGG | GAA | GAC | CCG | GCT | AAC | TTG | AGG | 1206 |
| Tyr | Asn | Ser | Gly | Tyr | Tyr | Tyr | Ser | Gly | Glu | Asp | Pro | Ala | Asn | Leu | Arg | |
| | 375 | | | | | 380 | | | | | 385 | | | | | |
| GTG | GTA | ACA | TCA | CAG | TCC | CCA | TAC | GTC | GTA | GTA | GCC | ACC | AAT | GCC | ATT | 1254 |
| Val | Val | Thr | Ser | Gln | Ser | Pro | Tyr | Val | Val | Val | Ala | Thr | Asn | Ala | Ile | |
| 390 | | | | | 395 | | | | | 400 | | | | | 405 | |
| GAG | TCA | GGG | GTA | ACG | CTG | CCA | GAT | TTA | GAT | ACA | GTT | GTT | GAC | ACA | GGT | 1302 |
| Glu | Ser | Gly | Val | Thr | Leu | Pro | Asp | Leu | Asp | Thr | Val | Val | Asp | Thr | Gly | |
| | | | | 410 | | | | | 415 | | | | | 420 | | |
| CTG | AAG | TGT | GAA | AAG | AGG | GTG | AGG | GTG | TCA | TCA | AAA | ATA | CCT | TTC | ATA | 1350 |
| Leu | Lys | Cys | Glu | Lys | Arg | Val | Arg | Val | Ser | Ser | Lys | Ile | Pro | Phe | Ile | |
| | | | 425 | | | | | 430 | | | | | 435 | | | |
| GTA | ACA | GGC | CTT | AAA | AGA | ATG | GCT | GTC | ACT | GTG | GGC | GAA | CAG | GCT | CAG | 1398 |
| Val | Thr | Gly | Leu | Lys | Arg | Met | Ala | Val | Thr | Val | Gly | Glu | Gln | Ala | Gln | |
| | | 440 | | | | | 445 | | | | | 450 | | | | |
| CGA | AGA | GGC | AGG | GTA | GGT | AGA | GTG | AAG | CCC | GGT | AGG | TAC | TAT | AGA | AGC | 1446 |
| Arg | Arg | Gly | Arg | Val | Gly | Arg | Val | Lys | Pro | Gly | Arg | Tyr | Tyr | Arg | Ser | |
| | 455 | | | | | 460 | | | | | 465 | | | | | |
| CAG | GAA | ACA | GCG | ACC | GGG | TCA | AAG | GAC | TAC | CAC | TAT | GAC | CTG | TTA | CAG | 1494 |
| Gln | Glu | Thr | Ala | Thr | Gly | Ser | Lys | Asp | Tyr | His | Tyr | Asp | Leu | Leu | Gln | |
| 470 | | | | | 475 | | | | | 480 | | | | | 485 | |
| GCA | CAC | AGG | TAT | GGG | ATA | GAA | GAT | GGA | ATC | AAC | GTG | ACA | AAG | TCC | TTT | 1542 |
| Ala | His | Arg | Tyr | Gly | Ile | Glu | Asp | Gly | Ile | Asn | Val | Thr | Lys | Ser | Phe | |
| | | | 490 | | | | | 495 | | | | | 500 | | | |
| AGG | GAA | ATG | AAT | TAC | GAT | TGG | AGC | CTG | TAC | GAG | GAG | GAC | AGC | TTG | CTG | 1590 |
| Arg | Glu | Met | Asn | Tyr | Asp | Trp | Ser | Leu | Tyr | Glu | Glu | Asp | Ser | Leu | Leu | |
| | | | 505 | | | | | 510 | | | | | 515 | | | |
| ATA | ACC | CAG | CTG | GAG | ATA | CTG | AAC | AAT | CTA | CTC | ATC | TCT | GAA | GAC | CTA | 1638 |
| Ile | Thr | Gln | Leu | Glu | Ile | Leu | Asn | Asn | Leu | Leu | Ile | Ser | Glu | Asp | Leu | |
| | | 520 | | | | | 525 | | | | | 530 | | | | |
| CCA | GCA | GCA | GTA | AAA | AAC | ATC | ATG | GCA | AGG | ACT | GAT | CAC | CCA | GAA | CCA | 1686 |
| Pro | Ala | Ala | Val | Lys | Asn | Ile | Met | Ala | Arg | Thr | Asp | His | Pro | Glu | Pro | |
| | 535 | | | | | 540 | | | | | 545 | | | | | |
| ATC | CAG | CTT | GCA | TAC | AAC | AGT | TAT | GAG | GTC | CAG | GTC | CCT | GTA | CTG | TTT | 1734 |
| Ile | Gln | Leu | Ala | Tyr | Asn | Ser | Tyr | Glu | Val | Gln | Val | Pro | Val | Leu | Phe | |
| 550 | | | | | 555 | | | | | 560 | | | | | 565 | |

| | | | | | | | | | | | | | | | | |
|---|---|---|---|---|---|---|---|---|---|---|---|---|---|---|---|---|
| CCA | AAA | ATA | AGG | AAT | GGG | GAG | GTT | ACA | GAT | ACT | TAC | GAG | AAC | TAC | TCA | 1782 |
| Pro | Lys | Ile | Arg | Asn 570 | Gly | Glu | Val | Thr | Asp 575 | Thr | Tyr | Glu | Asn | Tyr 580 | Ser | |
| TTC | CTA | AAT | GCA | AGA | AAA | CTA | GGG | GAA | GAT | GTA | CCT | GTG | TAC | ATT | TAT | 1830 |
| Phe | Leu | Asn | Ala 585 | Arg | Lys | Leu | Gly | Glu | Asp 590 | Val | Pro | Val | Tyr | Ile 595 | Tyr | |
| GCC | ACC | GAA | GAT | GAA | GAC | CTG | GCA | GTA | GAC | CTT | CTA | GGC | TTG | GAC | TGG | 1878 |
| Ala | Thr | Glu 600 | Asp | Glu | Asp | Leu | Ala 605 | Val | Asp | Leu | Leu | Gly 610 | Leu | Asp | Trp | |
| CCC | GAC | CCA | GGG | AAC | CAG | CAA | GTA | GTG | GAG | ACT | GGG | AAA | GCA | CTG | AAG | 1926 |
| Pro | Asp 615 | Pro | Gly | Asn | Gln | Gln 620 | Val | Val | Glu | Thr | Gly 625 | Lys | Ala | Leu | Lys | |
| CAA | GTG | GTA | GGA | CTG | TCC | TCT | GCT | GAG | AAT | GCC | CTG | CTC | ATA | GCC | CTG | 1974 |
| Gln 630 | Val | Val | Gly | Leu | Ser 635 | Ser | Ala | Glu | Asn | Ala 640 | Leu | Leu | Ile | Ala | Leu 645 | |
| TTT | GGG | TAT | GTA | GGA | TAT | CAA | GCT | TTG | TCA | AAA | AGA | CAC | GTC | CCA | ATG | 2022 |
| Phe | Gly | Tyr | Val | Gly 650 | Tyr | Gln | Ala | Leu | Ser 655 | Lys | Arg | His | Val | Pro 660 | Met | |
| ATC | ACA | GAC | ATA | TAC | ACC | ATA | GAA | GAT | CAA | AGA | CTA | GAG | GAC | ACA | ACC | 2070 |
| Ile | Thr | Asp | Ile 665 | Tyr | Thr | Ile | Glu | Asp 670 | Gln | Arg | Leu | Glu | Asp 675 | Thr | Thr | |
| CAC | CTC | CAA | TAT | GCA | CCT | AAT | GCT | ATA | AGA | ACT | GAG | GGG | AAG | GAG | ACT | 2118 |
| His | Leu | Gln 680 | Tyr | Ala | Pro | Asn | Ala 685 | Ile | Arg | Thr | Glu | Gly 690 | Lys | Glu | Thr | |
| GAA | CTA | AAG | GAA | TTA | GCA | GTG | GGT | GAC | ATG | GAC | AGA | ATC | ATG | GAA | TCC | 2166 |
| Glu | Leu 695 | Lys | Glu | Leu | Ala | Val 700 | Gly | Asp | Met | Asp | Arg 705 | Ile | Met | Glu | Ser | |
| ATC | TCA | GAT | TAT | GCA | TCA | GGA | GGG | TTG | ACA | TTC | ATA | AGA | TCT | CAG | GCA | 2214 |
| Ile 710 | Ser | Asp | Tyr | Ala | Ser 715 | Gly | Gly | Leu | Thr | Phe 720 | Ile | Arg | Ser | Gln | Ala 725 | |
| GAG | AAA | GTA | CGC | TAGCGGATCC | | | | | | | | | | | | 2236 |
| Glu | Lys | Val | Arg 730 | | | | | | | | | | | | | |

( 2 ) INFORMATION FOR SEQ ID NO:2:

( i ) SEQUENCE CHARACTERISTICS:
( A ) LENGTH: 729 amino acids
( B ) TYPE: amino acid
( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Gly | Leu | Glu | Thr 5 | Gly | Trp | Ala | Tyr | Thr 10 | His | Gln | Gly | Gly | Ile Ser 15 |
| Ser | Val | Asp | His 20 | Val | Thr | Ala | Gly | Lys 25 | Asp | Leu | Leu | Val | Cys 30 | Asp Ser |
| Met | Gly | Arg 35 | Thr | Arg | Val | Val | Cys 40 | Gln | Ser | Asn | Asn | Lys 45 | Leu | Thr Asp |
| Glu | Thr 50 | Glu | Tyr | Gly | Val | Lys 55 | Thr | Asp | Ser | Gly | Cys 60 | Pro | Asp | Gly Ala |
| Arg 65 | Cys | Tyr | Val | Leu | Asn 70 | Pro | Glu | Ala | Val | Asn 75 | Ile | Ser | Gly | Ser Lys 80 |
| Gly | Ala | Ala | Val | His 85 | Leu | Gln | Lys | Thr | Gly 90 | Gly | Glu | Phe | Thr | Cys Val 95 |
| Thr | Ala | Ser | Gly 100 | Thr | Pro | Ala | Phe | Phe 105 | Asp | Leu | Lys | Asn | Leu 110 | Lys Gly |
| Trp | Ser | Gly 115 | Leu | Pro | Ile | Phe | Glu 120 | Ala | Ser | Ser | Gly | Arg 125 | Val | Val Gly |

-continued

| | | | | | | | | | | | | | |
|---|---|---|---|---|---|---|---|---|---|---|---|---|---|
|Arg|Val|Lys|Val|Gly|Lys|Asn|Glu|Glu|Ser|Lys|Pro|Thr|Lys|Leu|Met|
| |130| | | |135| | | |140| | | | | |
|Ser|Gly|Ile|Gln|Thr|Val|Ser|Lys|Ser|Thr|Ala|Asp|Leu|Thr|Glu|Met|
|145| | | | |150| | | |155| | | | | |160|
|Val|Lys|Lys|Ile|Thr|Ser|Met|Asn|Arg|Gly|Asp|Phe|Lys|Gln|Ile|Thr|
| | | | |165| | | |170| | | | |175| |
|Leu|Ala|Thr|Gly|Ala|Gly|Lys|Thr|Thr|Glu|Leu|Pro|Lys|Ala|Val|Ile|
| | | |180| | | | |185| | | |190| | |
|Glu|Glu|Ile|Gly|Arg|His|Lys|Arg|Val|Leu|Val|Leu|Ile|Pro|Leu|Arg|
| | |195| | | |200| | | |205| | | | |
|Ala|Ala|Ala|Glu|Ser|Val|Tyr|Gln|Tyr|Met|Arg|Leu|Lys|His|Pro|Ser|
| |210| | | | |215| | | |220| | | | |
|Ile|Ser|Phe|Asn|Leu|Arg|Ile|Gly|Asp|Met|Lys|Glu|Gly|Asp|Met|Ala|
|225| | | | |230| | | |235| | | | |240| |
|Thr|Gly|Ile|Thr|Tyr|Ala|Ser|Tyr|Gly|Tyr|Phe|Cys|Gln|Met|Pro|Gln|
| | | |245| | | | |250| | | | |255| | |
|Pro|Lys|Leu|Arg|Ala|Ala|Met|Val|Glu|Tyr|Ser|Tyr|Ile|Phe|Leu|Asp|
| | |260| | | | |265| | | | |270| | | |
|Glu|Tyr|His|Cys|Ala|Thr|Pro|Glu|Gln|Leu|Ala|Val|Ile|Gly|Lys|Ile|
| |275| | | | |280| | | | |285| | | | |
|His|Arg|Phe|Ser|Glu|Ser|Ile|Arg|Val|Val|Ala|Met|Thr|Ala|Thr|Pro|
|290| | | | |295| | | | |300| | | | | |
|Ala|Gly|Ser|Val|Thr|Thr|Thr|Gly|Gln|Lys|His|Pro|Ile|Glu|Glu|Phe|
|305| | | | |310| | | | |315| | | | |320|
|Ile|Ala|Pro|Glu|Val|Met|Lys|Gly|Glu|Asp|Leu|Gly|Ser|Gln|Phe|Leu|
| | | |325| | | | |330| | | | |335| | |
|Asp|Ile|Ala|Gly|Leu|Lys|Ile|Pro|Val|Glu|Glu|Met|Lys|Gly|Asn|Met|
| | |340| | | | |345| | | | |350| | | |
|Leu|Val|Phe|Val|Pro|Thr|Arg|Asn|Met|Ala|Val|Asp|Val|Ala|Lys|Lys|
| |355| | | | |360| | | | |365| | | | |
|Leu|Lys|Ala|Lys|Gly|Tyr|Asn|Ser|Gly|Tyr|Tyr|Tyr|Ser|Gly|Glu|Asp|
|370| | | | |375| | | | |380| | | | | |
|Pro|Ala|Asn|Leu|Arg|Val|Val|Thr|Ser|Gln|Ser|Pro|Tyr|Val|Val|Val|
|385| | | | |390| | | | |395| | | | |400|
|Ala|Thr|Asn|Ala|Ile|Glu|Ser|Gly|Val|Thr|Leu|Pro|Asp|Leu|Asp|Thr|
| | | |405| | | | |410| | | | |415| | |
|Val|Val|Asp|Thr|Gly|Leu|Lys|Cys|Glu|Lys|Arg|Val|Arg|Val|Ser|Ser|
| | |420| | | | |425| | | | |430| | | |
|Lys|Ile|Pro|Phe|Ile|Val|Thr|Gly|Leu|Lys|Arg|Met|Ala|Val|Thr|Val|
| | |435| | | | |440| | | | |445| | | |
|Gly|Glu|Gln|Ala|Gln|Arg|Arg|Gly|Arg|Val|Gly|Arg|Val|Lys|Pro|Gly|
| |450| | | | |455| | | | |460| | | | |
|Arg|Tyr|Tyr|Arg|Ser|Gln|Glu|Thr|Ala|Thr|Gly|Ser|Lys|Asp|Tyr|His|
|465| | | | |470| | | | |475| | | | |480|
|Tyr|Asp|Leu|Leu|Gln|Ala|His|Arg|Tyr|Gly|Ile|Glu|Asp|Gly|Ile|Asn|
| | | |485| | | | |490| | | | |495| | |
|Val|Thr|Lys|Ser|Phe|Arg|Glu|Met|Asn|Tyr|Asp|Trp|Ser|Leu|Tyr|Glu|
| | |500| | | | |505| | | | |510| | | |
|Glu|Asp|Ser|Leu|Leu|Ile|Thr|Gln|Leu|Glu|Ile|Leu|Asn|Asn|Leu|Leu|
| | |515| | | | |520| | | | |525| | | |
|Ile|Ser|Glu|Asp|Leu|Pro|Ala|Ala|Val|Lys|Asn|Ile|Met|Ala|Arg|Thr|
| |530| | | | |535| | | | |540| | | | |
|Asp|His|Pro|Glu|Pro|Ile|Gln|Leu|Ala|Tyr|Asn|Ser|Tyr|Glu|Val|Gln|

```
545                       550                       555                       560

Val   Pro   Val   Leu   Phe   Pro   Lys   Ile   Arg   Asn   Gly   Glu   Val   Thr   Asp   Thr
                        565                      570                             575

Tyr   Glu   Asn   Tyr   Ser   Phe   Leu   Asn   Ala   Arg   Lys   Leu   Gly   Glu   Asp   Val
                  580                            585                       590

Pro   Val   Tyr   Ile   Tyr   Ala   Thr   Glu   Asp   Glu   Asp   Leu   Ala   Val   Asp   Leu
            595                          600                        605

Leu   Gly   Leu   Asp   Trp   Pro   Asp   Pro   Gly   Asn   Gln   Gln   Val   Val   Glu   Thr
      610                          615                              620

Gly   Lys   Ala   Leu   Lys   Gln   Val   Val   Gly   Leu   Ser   Ser   Ala   Glu   Asn   Ala
625                           630                        635                              640

Leu   Leu   Ile   Ala   Leu   Phe   Gly   Tyr   Val   Gly   Tyr   Gln   Ala   Leu   Ser   Lys
                        645                     650                              655

Arg   His   Val   Pro   Met   Ile   Thr   Asp   Ile   Tyr   Thr   Ile   Glu   Asp   Gln   Arg
                  660                     665                             670

Leu   Glu   Asp   Thr   Thr   His   Leu   Gln   Tyr   Ala   Pro   Asn   Ala   Ile   Arg   Thr
            675                           680                       685

Glu   Gly   Lys   Glu   Thr   Glu   Leu   Lys   Glu   Leu   Ala   Val   Gly   Asp   Met   Asp
      690                           695                 700

Arg   Ile   Met   Glu   Ser   Ile   Ser   Asp   Tyr   Ala   Ser   Gly   Gly   Leu   Thr   Phe
705                           710                       715                             720

Ile   Arg   Ser   Gln   Ala   Glu   Lys   Val   Arg
                  725
```

( 2 ) INFORMATION FOR SEQ ID NO:3:

( i ) SEQUENCE CHARACTERISTICS:
        ( A ) LENGTH: 240 base pairs
        ( B ) TYPE: nucleic acid
        ( C ) STRANDEDNESS: double
        ( D ) TOPOLOGY: linear     ( i i ) MOLECULE TYPE: cDNA     ( v i ) ORIGINAL SOURCE:
        ( A ) ORGANISM: Bovine viral diarrhea virus
        ( B ) STRAIN: Osloss     ( i x ) FEATURE:
        ( A ) NAME/KEY: CDS
        ( B ) LOCATION: 1..240
        ( D ) OTHER INFORMATION: /partial
            / product= "P80 epitope region"

( x i ) SEQUENCE DESCRIPTION: SEQ ID NO:3:

```
GGA   TAT   CAA   GCT   TTG   TCA   AAA   AGA   CAC   GTC   CCA   ATG   ATC   ACA   GAC   ATA      48
Gly   Tyr   Gln   Ala   Leu   Ser   Lys   Arg   His   Val   Pro   Met   Ile   Thr   Asp   Ile
 1                            5                             10                          15

TAC   ACC   ATA   GAA   GAT   CAA   AGA   CTA   GAG   GAC   ACA   ACC   CAC   CTC   CAA   TAT      96
Tyr   Thr   Ile   Glu   Asp   Gln   Arg   Leu   Glu   Asp   Thr   Thr   His   Leu   Gln   Tyr
                  20                            25                            30

GCA   CCT   AAT   GCT   ATA   AGA   ACT   GAG   GGG   AAG   GAG   ACT   GAA   CTA   AAG   GAA     144
Ala   Pro   Asn   Ala   Ile   Arg   Thr   Glu   Gly   Lys   Glu   Thr   Glu   Leu   Lys   Glu
            35                            40                            45

TTA   GCA   GTG   GGT   GAC   ATG   GAC   AGA   ATC   ATG   GAA   TCC   ATC   TCA   GAT   TAT     192
Leu   Ala   Val   Gly   Asp   Met   Asp   Arg   Ile   Met   Glu   Ser   Ile   Ser   Asp   Tyr
      50                            55                            60

GCA   TCA   GGA   GGG   TTG   ACA   TTC   ATA   AGA   TCT   CAG   GCA   GAG   AAA   GTA   AGA     240
Ala   Ser   Gly   Gly   Leu   Thr   Phe   Ile   Arg   Ser   Gln   Ala   Glu   Lys   Val   Arg
65                            70                            75                          80
```

( 2 ) INFORMATION FOR SEQ ID NO:4:

( i ) SEQUENCE CHARACTERISTICS:
   ( A ) LENGTH: 80 amino acids
   ( B ) TYPE: amino acid
   ( D ) TOPOLOGY: linear ( i i ) MOLECULE TYPE: protein ( x i ) SEQUENCE DESCRIPTION: SEQ ID NO:4:

```
Gly Tyr Gln Ala Leu Ser Lys Arg His Val Pro Met Ile Thr Asp Ile
 1               5                  10                  15

Tyr Thr Ile Glu Asp Gln Arg Leu Glu Asp Thr Thr His Leu Gln Tyr
            20                  25                  30

Ala Pro Asn Ala Ile Arg Thr Glu Gly Lys Glu Thr Glu Leu Lys Glu
         35                  40                  45

Leu Ala Val Gly Asp Met Asp Arg Ile Met Glu Ser Ile Ser Asp Tyr
     50                  55                  60

Ala Ser Gly Gly Leu Thr Phe Ile Arg Ser Gln Ala Glu Lys Val Arg
 65                  70                  75                  80
```

METHOD OF DETECTING BOVINE DIARRHOEA VIRUS INFECTION, NUCLEOTIDE SEQUENCE ENCODING A PROTEIN INDUCED BY THIS VIRUS INFECTION AND RECOMBINANT PROTEINS AND ANTIGENS RELATING THERETO

This application is a continuation of application Ser. No. 07/895,999 filed Jun. 11, 1992, now abandoned.

Method for detecting bovine diarrhoea virus infection, nucleotide sequence encoding a protein induced by this virus infection and recombinant proteins and antigens relating thereto.

BACKGROUND OF THE INVENTION

1. Field of the Invention

The present invention relates to a method for detecting bovine diarrhoea virus infection, a nucleotide sequence encoding a protein associated with this virus infection and recombinant proteins and antigens relating thereto.

2. Description of the Prior Art

Bovine diarrhoea virus (BVD) is an infectious single-stranded RNA-containing enveloped virus which is related to the conventional hog cholera virus and to the Border disease virus, the three viruses forming the Pestivirus genus which belongs to the Togaviridae family. The BVD virus is universally distributed in bovine populations and manifests itself by a wide range of clinical symptoms associated with congenital, respiratory or enteric diseases (bovine viral diarrhoea, mucosal disease).

Isolates of BVD viruses may be classified into two distinct categories or biotypes according to their effects during cell culture: cytopathogenic and noncytopathogenic.

Acute infection of seronegative animals is normally benign or subclinical. On the other hand, intrauterine infection of the foetus, during approximately the first four months after the start of pregnancy, by a noncytopathogenic strain can not only produce abortions, still births or the birth of weak calves, but also the birth of calves having persistent viremia, that is to say permanently excreting the virus. This period of four months corresponds to an absence of immunity in the foetus. When the immune system then becomes competent, it recognises the virus as its own and a situration of immunotolerance is established (absence of antibodies). These animals will not be able to survive a subsequent infection by a cytopathogenic strain of homologous BVD virus.

Maintenance of the noncytopathogenic virus within the bovine population is ensured by its slow dissemination following acute infection of seronegative animals and, in particular, by its continual excretion by animals having persistent viremia. (See J. Brownlie et al., Ann. Rech. Vet. (1987) 18:157–166).

A. Fenton et al. (Journal of Virological Methods, 27 (1990), 253–260) detect the Pestivirus antigens in the blood of viremic sheep infected in a persistent manner by the Border disease virus, by an ELISA carried out so as to detect a specific antigen in the leucocytes of these animals. This technique requires prior purification of the leucocytes, which proves to be long and complex to carry out.

The genome of the Osloss viral strain, of cytopathogenic biotype, has been cloned and completely sequenced by Renard et al. (Patent Application EP-A-0,208,672 of 8 July 1985). The Applicant has found that the open reading frame (ORF) of the BVD Osloss genomic sequence, which is 12408 nucleotides in length, has a coding capacity of 3951 amino acids (aas).

In an abstract distributed during the symposium on ruminant infections by Pestiviruses which was held at Hanover on 8 and 9, June 1990, C. Lecomte et al. indicate the identification of a cDNA translational product of the BVD virus immunoprecipitated by monoclonal antibodies recognising the nonstructural protein p80 of a certain number of Pestivirus strains. The same cDNA is expressed in $E.$ $coli$ and the antigen produced is used in competition ELISA to detect anti-BVD antibodies in the bovine serum.

The preparation and the characterisation of a series of monoclonal antibodies have been described by C. Lecomte et al. (Veterinary Microbiology, 23 (1990), 193–201), as well as the use of a fusion protein produced in $E.$ $coli$ as recombinant antigen enabling anti-BVD serum antibodies to be detected in a competition ELISA with the chosen monoclonal antibodies.

In an abstract distributed at the VIIIth internalional Congress of Virology which was held in Berlin on 26 to 31 August 1990, C. Lecomte et al. proposed the use of two ELISA tests for the detection on the one hand of anti-BVD antibodies and, on the other hand, of viral antigens. The anti-BVD antibodies in the serum would be detected by a competition ELISA using a BVD Osloss recombinant antigen p80 produced in $E.$ $coli$ and monoclonal antibodies specifically directed against the p80 protein of a certain number of Pestivirus strains. The second ELISA would be a sandwich type ELISA using two monoclonal antibodies and which would permit the detection of antigens in persistent viremic animals.

However, the Applicant has found that the p80 protein produced in $E.$ $coli$ is not recognised by all the anti-p80 monoclonal antibodies and especially by some of those exhibiting polyspecificity, that is to say reacting towards several or all Pestivirus strains, which undermines the chances of being able to detect in a single operation any infection by any BVD strain, all the more so as the second ELISA, based on the use of two monoclonal antibodies, could also not be sufficiently polyspecific.

SUMMARY OF THE INVENTION

The objective of the invention is to provide a very sensitive method of detection permitting a complete and effective control of infection which may be caused in livestock by a BVD virus of any type, and relating to both the detection of persistent viremias and acute infections.

The subject of the invention is therefore a method for detecting infection of a blood sample by the BVD virus, comprising a first test for the detection of anti-BVD antibodies and a second test for the detection of viral particles, characterised in that the anti-p80 antibodies are detected by means of a recombinant antigen comprising the BVD virus nonstructural protein p80, produced in a eukaryotic host, and preferably an anti-p80 monoclonal antibody used as competing antibody, and in that the presence of viral particles is detected by means of polyclonal or monoclonal antibodies directed against the BVD virus protein p80, and preferably of a serum directed against the recombinant p80 antigen produced in a eukaryotic or prokaryotic host, for the detection of persistent viremias and acute infections by any BVD strain.

The p80 protein is preferably derived from BVD Osloss and the nucleotide sequence encoding this protein has been completely sequenced. The sequence is given in the attached list of sequences, under the reference SEQ ID No: 1. The Applicant has thus advantageously located one potential cleavage site of p80 (KVR: lysine—valine—arginine) corresponding to the end of p80.

The p80 protein is expressed in viral or eukaryotic vectors, and especially in the Vaculovirus system, which is advantageously the vaculovirus AcNPV (Autographa californica nuclear polyhedrosis virus).

The p80-encoding nucleotide sequence is introduced into an appropriate expression vector according to known techniques for constructing these vectors, especially those described in Patent Application EP-A-0,208,672.

Of course, the abovementioned nucleotide sequence includes all equivalent sequences, that is to say, which possess the essential properties of the sequence. By way of example, this would be the case for a sequence encoding an identical amino acid sequence, but which would use other specific codons by degeneration of the code. This would also be the case for a sequence encoding an amino acid sequence which is no longer identical but similar, taking into account the similarities between amino acids.

Equivalent sequence is also understood to mean a p80-encoding sequence derived from another BVD strain and maintaining recognition by anti-p80 antibodies.

The recombinant antigen is itself obtained from cultures of eukaryotic host cells which have been transfected with the p80-expressing vector, and preferably may be animal or yeast, especially Saccharomyces cerevisiae, cell cultures. The transfer vectors for recombinants to be selected for example by resistance to antibiotics or by other known means of selection (Broach J. et al., Meth. Enz. (1983) 101:307). For the promoters, see also Hess et al., J. Adv. Enz. Reg. (1968) 7/149, and Holland et al., Biochemistry (1968) 17:4900 or Itzeman et al., J. Biol. Chem. (1980) 255:2073.

The animal cells are, preferably, known mammalian cell lines such as HeLa, CHO or BHK, insect cells, for example Spodoptera frugiperda (deposit ATCC CRL 1711, Sf9) (especially for the Baculovirus system) and, in general, lines whose use for the expression of substances to be administered to animals has been recognised by the health authorities, will be preferred. Viral promoters such as those of he SV40 virus (Fiers et al., Nature, megalovirus (McGregor and Caskey, Nucleic Acids Res. 17:2365, 1989), or alternatively, that of the polyhodrin gene of the Baculovirus AcNPV or Autographa californica nuclear polyhedrosis virus (Hooft van Iddekinge et al., 1983, Virology 131:561–565), will be used as promoter in these cellular constructs.

The recombinant antigen is preferably immobilised on a solid support (for example microtitre plates), especially via an anti-p80 monoclonal antibody which is used as captor. Dilutions of bovine sera are placed in contact with the immobilised or nonimmobilised antigen and the anti-BVD antibodies are either directly revealed by a bovine anti-IgG antiserum coupled for example to peroxidase or biotin (indirect ELISA), or revealed by competition ELISA with a second anti-p80 monoclonal antibody coupled for example to peroxidase or biotin. In fact this detection may be carried out on any bovine blood fraction, especially serum and plasma.

Preferably, the viral particles in crude or white blood cell-enriched whole blood are revealed by mere centrifugration, especially for 30 minutes at 2500 g.

In order to ensure complete detection of the presence of viral particles of all the BVD types, a mixture of three p80-specific monoclonal antibodies is preferably used as captor instead of a single monoclonal antibody.

A sandwich type ELISA is preferably carried out using, as captor, the mixture of three viral p80-specific monoclonal antibodies, and as stain, the serum directed against the recombinant p80 protein. The serum is derived in particular from the immunisation of animals, in particular rabbits or goats, by repeated inoculations of recombinant p80 which may be produced both in prokaryotic and eukaryotic cells.

Samples corresponding to a viral titre of less than for example $10^3$ pfu/ml (pfu=plaque-forming units) may thus be detected as positive. In effect, the invention makes it possible to detect as positive, samples which, by the normal method of immunofluorescence on infected cells, may require three successive passages of the virus and the choice of appropriate host cells, which makes it necessary to propagate the virus on several cell types.

Since the p80 protein does not contain neutralisation epitopes, this method advantageously enables a distinction to be made between animals infected naturally and animals vaccinated with a recombinant vaccine based on the structural proteins of the virus.

The subject of the invention is also the nucleotide sequence with the reference SEQ ID No: 1 which corresponds to the BVD Osloss sequence encoding the nonstructural protein p80, or an equivalent sequence according to the definition given above, as well as any new nucleotide sequence containing it and comprising means permitting its expression or associated with such means.

The subject of the invention is also the recombinant p80 protein corresponding to the translation of this sequence, especially in a eukaryotic host, in the abovementioned expression systems, and any recombinant antigen containing this sequence, especially consisting of extracts of host cells, in particular eukaryotic cells, as stated above.

DESCRIPTION OF THE PREFERRED EMBODIMENTS

I—LOCATION AND SEQUENCING OF THE SEQUENCE ENCODING p80.

Figure 1:
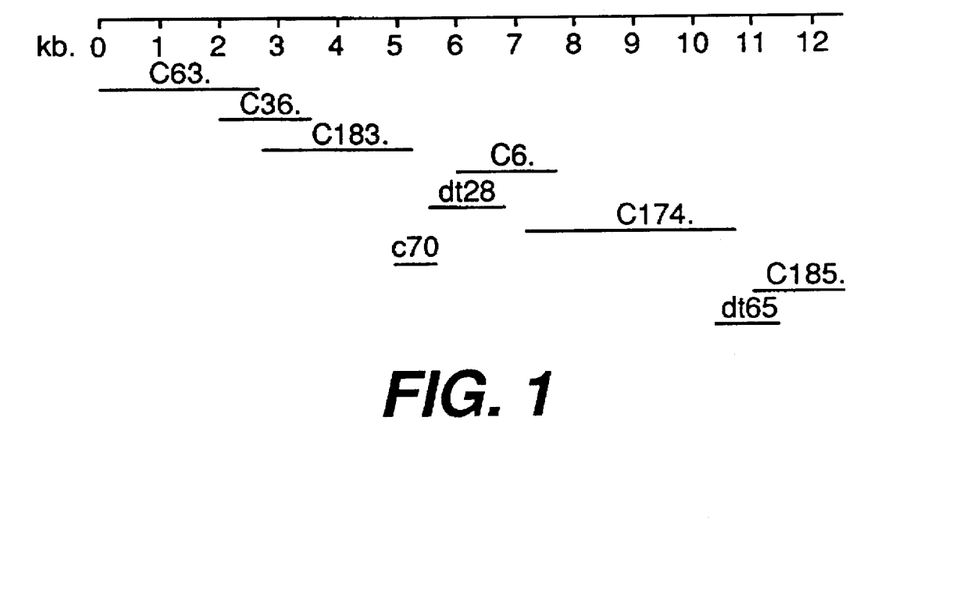
FIG. 1 shows the position of the cDNA clones spanning the entire genome of the BVD virus (Osloss strain).

1. The cDNA C174 was cloned (pcP 174 clone from the cDNA library described in European Patent Application EP-A-0,208,672) (FIG. 1) into the plasmid oSP65, downstream of the RNA polymerase promoter of the bacteriophage SP6, between the EcoRI and BamHI sites (vector described by Melton D. A. et al., 1984, Nucleic Acids Res. 12:7035–7056).

Figure 2:
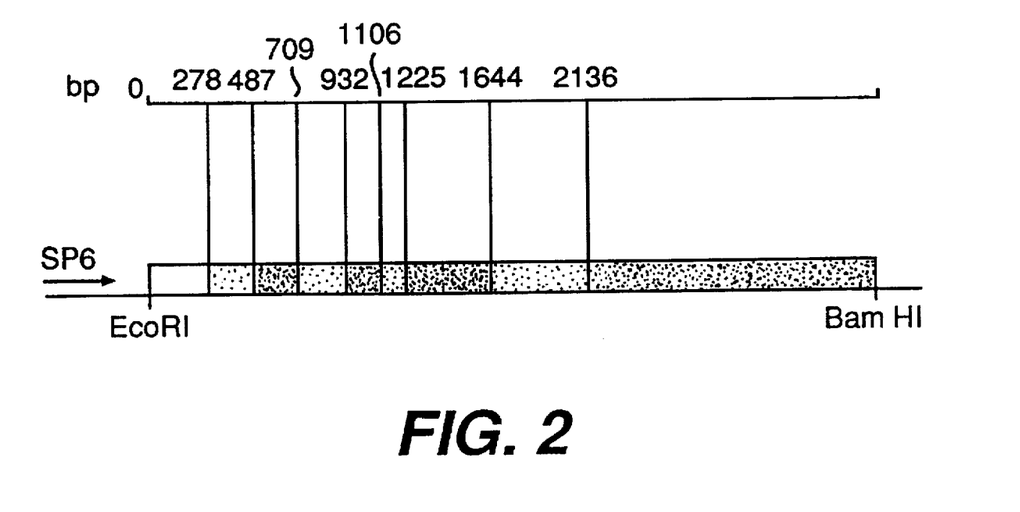
FIG. 2 shows the analysis in vitro of the region of the BVD Osloss genome corresponding to the cDNA clone 174. The number therein indicate the size (base pairs=bp) of the various fragments obtained by digestion of the 174 insert by each of the restriction enzymes used.

2. After digestion with various restriction enzymes whose position of successive sites is indicated in FIG. 2, each fragment obtained was transcribed in vitro and then translated in an acellular system (lysate of rabbit reticulocytes). The translational products of increasing molecular weight were immuno-precipitated with anti-p80 monoclonal antibodies; this made it possible to locate an immunoreactive region 80 amino acids in length, which is located in FIG. 3 and whose sequence is given in the list of sequences under the reference SEQ ID No: 3.

Figure 4:
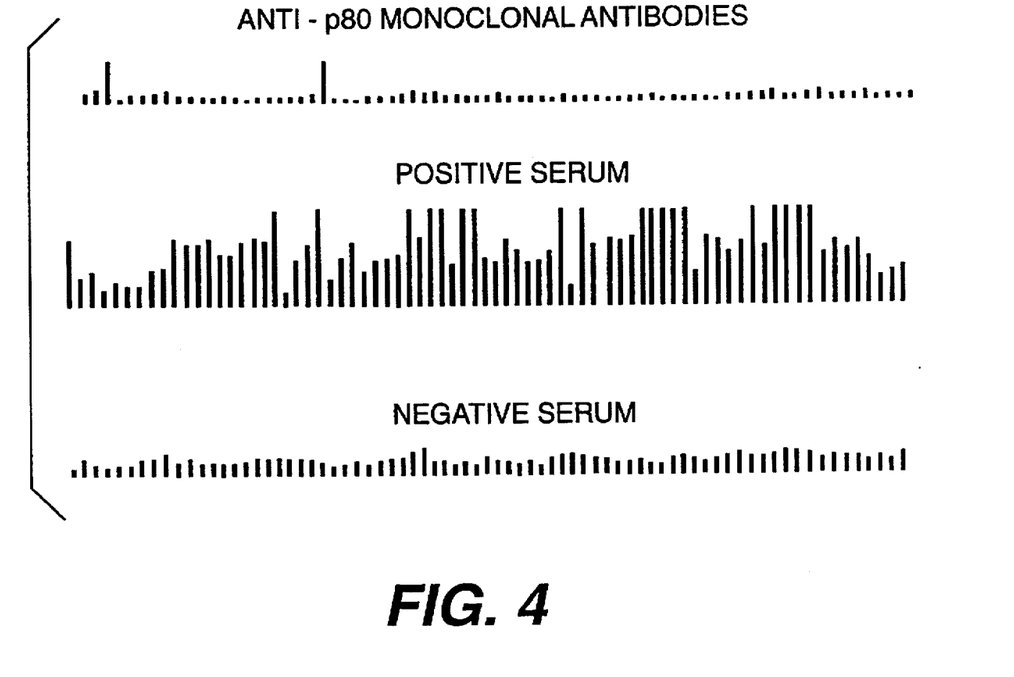
FIG. 4 shows the screening of epitopes in the immunoreactive region, which is 80 amino acids in length, situated with the p80 protein.

3. The presence of recognised epitopes in this region of 80 amino acids was confirmed by epitope scanning, that is to say that 75 peptide hexamers spanning this region were synthesised on a solid support and tested by ELISA in the presence of anti-p80 monoclonal antibodies and antibody-positive or negative bovine sera. The result is illustrated in FIG. 4.

4. Following the location of the anti-p80 epitopes, the sequence encoding the p80 protein was reconstituted so as to resemble the natural protein as much as possible. The presence of one potential cleavage site (KVR: lysine—valine—arginine) corresponding to the end of p80 was determined by analysis of the genomic sequence of the BVD/Osloss virus and by comparison with that of known Flaviviridae; the theoretical molecular weight of the protein between these two sites if 80430 daltons. The first of the two triplets occurs exactly at the same position in the genome of the BVD/NADL virus, and the entire BVD/Osloss genome contains only 5 KVR triplets all situated in the portion encoding the nonstructural proteins of the virus (the NADL genome contains only three of them).

Figure 3:
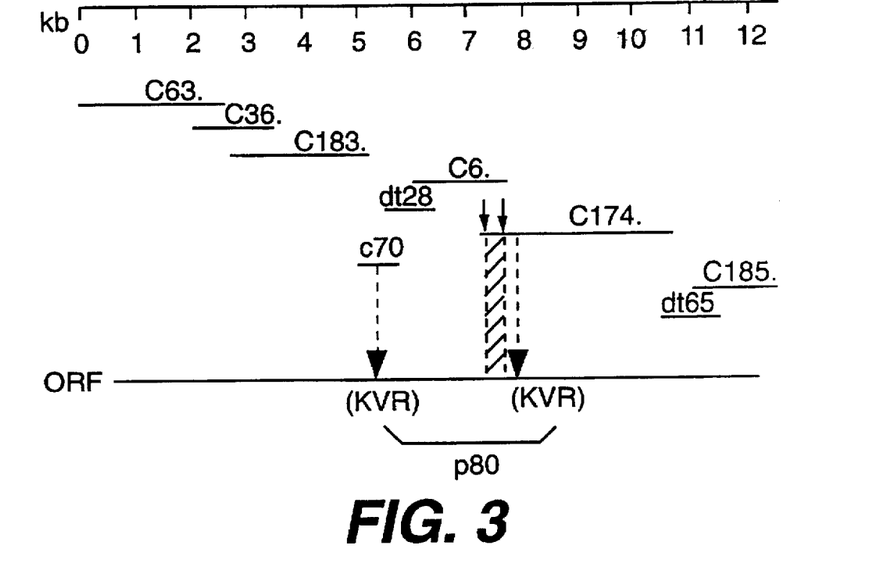
FIG. 3 shows the location, on the BVD Osloss genome, of the immonoreactive region of 80 amino acids and limits of the p80 protein.

The p80 fragment of 2200 bp (base pairs) corresponding to the p80-encoding sequence was amplified by PCR (polymerase chain reaction) and cloned; its location is illustrated in FIG. 3; its nucleotide sequence has the reference SEQ ID No: 1.

II—EXPRESSION OF THE RECOMBINANT ANTIGEN

Figure 5:
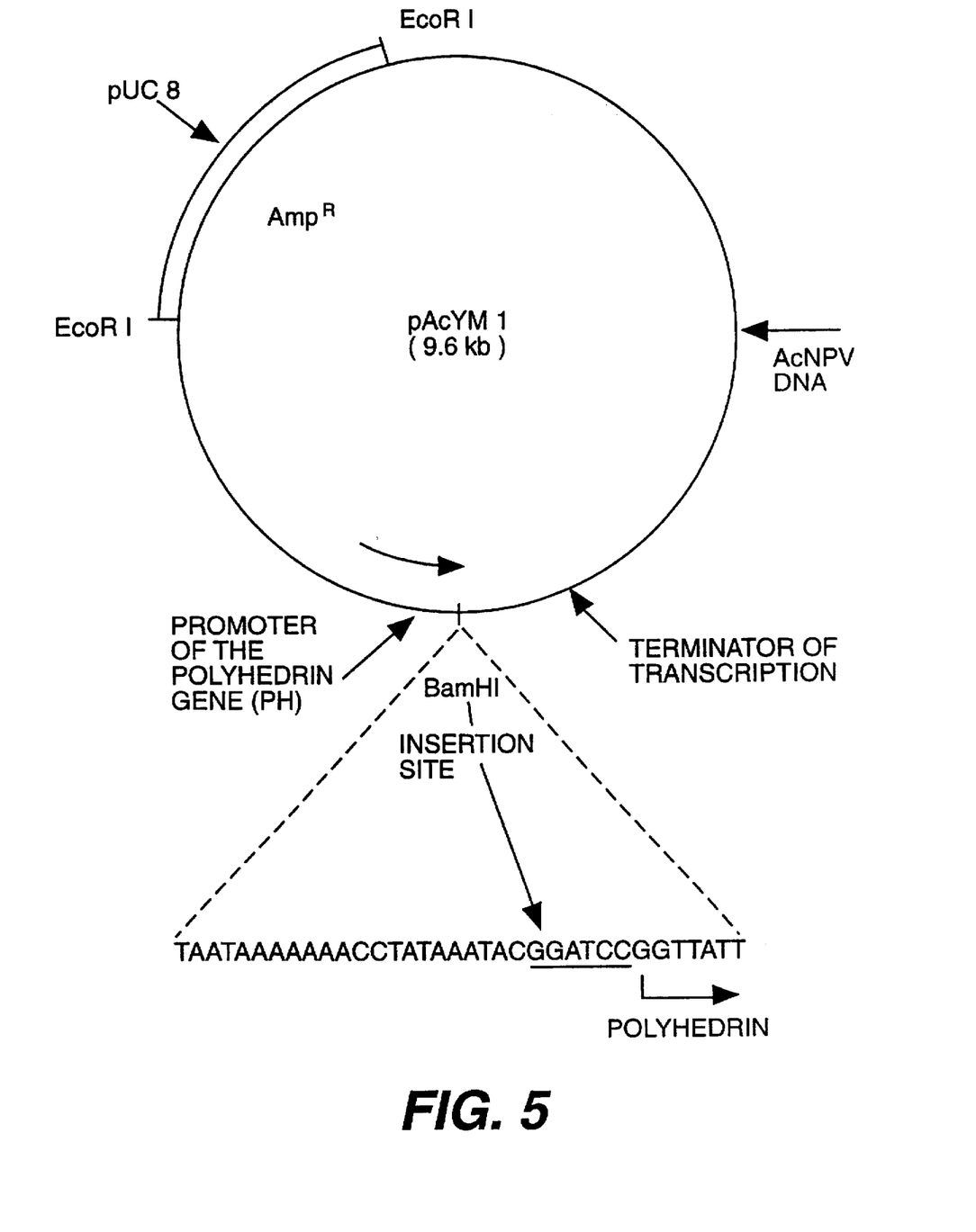
FIG. 5 shows the map of the transfer vector pAcYM1 described by Matsuura et al. in J. Gen. Virol. (1987), 68:1233 to 1250.

The integration of the p80 fragment into the genome of the *Baculovirus Autographa* californica nuclear polyhedrosis virus (AcNPV) was carried out via the transfer vector pAcYM1 described by Matsurra et al. (J. Gen. Virol. 68:1233–1250, 1987; restriction map in FIG. 5) downstream of the promoter of the AcNPV polyhedrin gene. This vector contains the polyadenylation sito of the polyhodrin gene as well as the gene for resistance to ampicillin and the replication origin of the plasmid pUC8 (J. Messing, 1983, Meth. Enzymol. 101:20).

To this effect, the amplified fragment of the sequence SEQ ID No: 1 is digested with the restriction enzymes NcoI and BamHI and then treated with DNA polymerase (Klenow fragment) so as to make the 5' and 3'ends of the fragment blunt. It is them cloned into the BamHI-digested vector pAcYM1 and treated with DNA polymerase (Klenow fragment) so as to make the ends blunt. The recombinant plasmid pAcYM1-p80 is obtained, p80 being expressed under the control of the promoter of the polyherin gene.

The plasmid obtained is used to cotransfect the insect cells Sf9 together with the DNA purified from the wild type AcNPV. A recombinant virus AcNPV-p80 was purified by plating the cotransfection supernatnat and isolating the viral plaques by covering the agarose.

III—ELISA TEST FOR DETECTING ANTI-p80 ANTIBODIES

Principle:

The test is based on the detection of anti-p80 antibodies, in other words, antibodies directed against a nonstructural protein of 80,000 daltons associated with infection by the BVD virus.

A recombinant antigen comprising the p80 protein derived from the Osloss virus is bound to a solid support via a monoclonal antibody which is used as captor. The bovine blood or serum sample is placed in contact with the bound antigen and is them either directly revealed by a coupled bovine anti-IgG antiserum, or placed in competition with a second coupled anti-p80 monoclonal antibody.

Materials, reagents and samples:

1. Materials and buffers:
   —96-well ELISA plates (NUNC—MAXISORP);
   —carbonate buffer, pH 9.6; 15 mM $Na_2Co_3$, 35 mM $NaHCO_3$, 3 mM $NaN_3$;
   —wash buffers: (1) PBS, (2) PBS, 0.1% Tween 20;
   —dilution buffer: PBS, 0.1% Tween 20, 10% horse serum (assessed to be free of BVD virus);
   —saturation buffer: PBS, 10% horse serum (assessed to be free of BVD virus);
   —chromogen and appropriate buffer.

2. Reagents:
   —1 anti-p80 monoclonal antibody used as captor of the antigen p80 (dilute ascites liquid);
   —recombinant p80 antigen;
   —a) competition ELISA: 1 anti-p80 monoclonal antibody diluted and coupled to peroxidase or biotin;
   —b) indirect ELISA: bovine anti-IgG serum (rabbit or goat) coupled to peroxidase or biotin.

3. Preparation of the samples:
   —serum samples: collection of blood in tubes without anticoagulant; coagulation minimum 4 hours at room temperature; centrifugation 2500 g, 30 minutes; collect the supernatnat=serum;
   —the test may be carried out on any blood fraction, especially plasma or even whole blood collected in tubes with anticoagulant.

Method:

1. Binding of the captor:

The dilute anti-p80 monoclonal antibody is distributed in an amount of 100 µl per well:
   —contact overnight at 4° C.;
   —3 washes with buffer (1).

2. Saturation (optional):
150 µl/well of saturation buffer:
   —1 hour at 37° C.

3. Binding of the antigen:
recombinant p80 antigen (100 µl/well)
   —contact overnight at 4° C.

4. Contact with the samples:
100 µl/well; sera diluted 10×:
   —contact 2 hours at 37° C., 5. Contact with the staining antibody:
a) Competition ELISA: contact with dilute and coupled monoclonal antibody:
   1 h 30 min at 37° C.;
   3 washes with buffer (2);
   3 washes with water.

b) Indirect ELISA: contact with dilute and coupled bovine anti-IgG serum;
   1 h 30 min at 37° C.;
   3 washes with buffer (2);
   3 washes with water.

6. Staining with the chromogen:
The procedure varies according to the chromogen and is detailed by its supplier.

IV—ELISA TEST FOR DETECTING VIRAL PARTICLES.

Principle:

The test is based on the detection of the p80 protein, a nonstructural protein of the BVD virus which is present in a large amount in the blood of infected animals. A mixture of three monoclonal antibodies specific for this p80 protein is used as captor and bound to the solid support (microtitre plates). Whole blood or the fraction of blood enriched with white blood cells or "buffy coat" is placed in contact with the bound captor mixture. A serum (rabbit or goat), directed against the recombinant p80 protein, is used as staining antibody either directly coupled (to peroxidase or biotin), or itself stained with a second antibody (rabbit or goat anti-IgG) coupled to peroxidase or biotin.

The presence of viral antigen in the tested samples is indicated by the increase in the initial optical density in the presence of chromogen.

Materials, reagents and samples:
1. Materials and buffers:
—96-well ELISA plates: NUNC-MAXISORP;
—carbonate buffer, pH 9.6: 15 mM $Na_2CO_3$, 35 mM $NaHCO_3$, 3 mM $NaN_3$;
—wash buffer: PBS, 0.1% Tween 20;
—saturation/dilution buffer: PBS, 0.1% Tween 20, 10% horse serum (assessed to be free of BVD virus);
—chromogen and appropriate buffer.

2. Reagents:
—mixture of 3 anti-p80 monoclonal antibodies, dilute ascites liquids;
—serum (rabbit or goat) directed against the recombinant p80 protein, either directly coupled (to peroxidase or biotin), or itself stained with a second antibody (rabbit or goat anti-IgG) coupled to peroxidase or biotin.

3. Preparation of the samples:
Collection of blood in heparinised tubes; the samples are tested either as they are, or after enrichment with white blood cells according to the following procedure: centrifugation at 2500 g; 30 minutes; after centrifugation, removing the upper layer consisting of plasma by pipetting, and collecting the buffy coat, a whitish zone situated between the plasma and the red blood cells.

Method:
1. Binding of the captor:
Mixture of monoclonal antibodies diluted and distributed in an amount of 100 µl per well;
—contact overnight at 4° C.;
—3 washes in PBS/Tween.

2. Saturation:
150 µl well of saturation buffer containing 10% of horse serum;
—1 hour at 37° C.

3. Contact with the samples:
100 µl of whole blood or buffy coat per well;
—contact 2 hours in PBS/Tween.
—3 washes in PBS/Tween.

4. Contact with the staining antibody:
Dilute anti-p80 serum, coupled or uncoupled (peroxidase or biotin):
—contact 1 h at 37° C. (100 µl/well);
—3 washes in PBS/Tween;
—3 washes with water;
If uncoupled serum is used, repeat contact with coupled antiserum (1 hour at 37° C.).

5. Staining with the chromogen:
The procedure varies according to the chromogen chosen and is detailed by its supplier.

LIST OF SEQUENCES.

SEQ ID No: 1

TYPE OF SEQUENCE: nucleotide sequence
LENGTH OF SEQUENCE: 2236 base pairs
NUMBER OF STRANDS: single
CONFIGURATION: linear
TYPE OF MOLECULE: cDNA for genomic RNA
ORIGIN: BVD Osloss
REGION TRANSLATED: 40-2229
PROPERTIES: encodes the protein p80

```
                                                           Met Gly Leu    3
TCT AGA AAT TTT GTT TAA CTT TAA GAA GGA GAT ATA CCC ATG GGA CTG     48
 XbaI                                                NcoI

Glu Thr Gly Trp Ala Tyr Thr His Gln Gly Gly Ile Ser Ser Val Asp    19
GAA ACC GGA TGG GCC TAC ACA CAC CAA GGC GGC ATA AGC TCA GTA GAC    96

His Val Thr Ala Gly Lys Asp Leu Leu Val Cys Asp Ser Met Gly Arg    35
CAT GTG ACC GCA GGC AAA GAC CTA CTG GTT TGT GAT AGT ATG GGT AGG   144

Thr Arg Val Val Cys Gln Ser Asn Asn Lys Leu Thr Asp Glu Thr Glu    51
ACA AGA GTG GTT TGC CAA AGT AAC AAC AAG TTA ACT GAT GAG ACA GAA   192

Tyr Gly Val Lys Thr Asp Ser Gly Cys Pro Asp Gly Ala Arg Cys Tyr    67
TAT GGT GTC AAG ACG GAC TCC GGA TGT CCA GAT GGT GCC AGG TGC TAC   240

Val Leu Asn Pro Glu Ala Val Asn Ile Ser Gly Ser Lys Gly Ala Ala    83
GTA TTA AAT CCA GAG GCA GTA AAT ATA TCA GGG TCC AAG GGA GCT GCT   288

Val His Leu Gln Lys Thr Gly Gly Glu Phe Thr Cys Val Thr Ala Ser    99
GTA CAC CTC CAA AAA ACA GGT GGG GAA TTC ACA TGT GTT ACT GCA TCG   336

Gly Thr Pro Ala Phe Phe Asp Leu Lys Asn Leu Lys Gly Trp Ser Gly   115
GGA ACT CCA CCC TTC TTT GAC CTG AAA AAT TTG AAG GGA TGG TCA GGT   384
```

-continued
LIST OF SEQUENCES.

| | | | | | | | | | | | | | | | |
|---|---|---|---|---|---|---|---|---|---|---|---|---|---|---|---|
| Leu | Pro | Ile | Phe | Glu | Ala | Ser | Ser | Gly | Arg | Val | Val | Gly | Arg | Val | Lys | 131 |
| CTA | CCC | ATA | TTT | GAG | GCT | TCT | AGT | GGC | AGG | GTG | GTC | GGC | AGA | GTT | AAA | 432 |

```
Leu Pro Ile Phe Glu Ala Ser Ser Gly Arg Val Val Gly Arg Val Lys    131
CTA CCC ATA TTT GAG GCT TCT AGT GGC AGG GTG GTC GGC AGA GTT AAA    432

Val Gly Lys Asn Glu Glu Ser Lys Pro Thr Lys Leu Met Ser Gly Ile    147
GTA GGA AAG AAT GAG GAA TCC AAT CCC ACA AAA TTA ATG AGT GGT ATC    480

Gln Thr Val Ser Lys Ser Thr Ala Asp Leu Thr Glu Met Val Lys Lys    163
CAA ACC GTC TCA AAA AGC ACA GCC GAT TTA ACA GAG ATG GTC AAG AAG    528

Ile Thr Ser Met Asn Arg Gly Asp Phe Lys Gln Ile Thr Leu Ala Thr    179
ATA ACC AGC ATG AAC AGG GGA GAC TTT AAG CAG ATA ACC CTT GCA ACA    576

Gly Ala Gly Lys Thr Thr Glu Leu Pro Lys Ala Val Ile Glu Glu Ile    195
GGG GCA GGA AAA ACT ACA GAA CTC CCA AAG GCA GTG ATA GAG GAG ATA    624

Gly Arg His Lys Arg Val Leu Val Leu Ile Pro Leu Arg Ala Ala Ala    211
GGA AGA CAC AAG CGG GTG CTA GTG CTT ATA CCA TTG AGA GCA GCA GCT    672

Glu Ser Val Tyr Gln Tyr Met Arg Leu Lys His Pro Ser Ile Ser Phe    227
GAG TCA GTC TAT CAA TAC ATG AGA TTG AAA CAT CCC AGT ATC TCC TTC    720

Asn Leu Arg Ile Gly Asp Met Lys Glu Gly Asp Met Ala Thr Gly Ile    243
AAC TTA AGA ATA GGG GAC ATG AAA GAA GGG GAC ATG GCA ACT GGG ATC    768

Thr Tyr Ala Ser Tyr Gly Tyr Phe Cys Gln Met Pro Gln Pro Lys Leu    259
ACC TAC GCC TCA TAT GGA TAT TTT TGC CAA ATG CCG CAG CCG AAG CTC    816

Arg Ala Ala Met Val Glu Tyr Ser Tyr Ile Phe Leu Asp Glu Tyr His    275
AGG GCC GCA ATG GTA GAG TAT TCA TAC ATA TTT CTG GAT GAG TAT CAC    864

Cys Ala Thr Pro Glu Gln Leu Ala Val Ile Gly Lys Ile His Arg Phe    291
TGT GCT ACT CCT GAG CAG TTG GCT GTC ATA GGA AAA ATT CAC AGA TTT    912

Ser Glu Ser Ile Arg Val Val Ala Met Thr Ala Thr Pro Ala Gly Ser    307
TCT GAA AGC ATA AGG GTG GTT GCT ATG ACC GCC ACC CCA GCA GGG TCA    960

Val Thr Thr Thr Gly Gln Lys His Pro Ile Glu Glu Phe Ile Ala Pro    323
GTA ACT ACA ACA GGG CAA AAA CAC CCA ATA GAA GAA TTC ATA GCT CCT    1008

Glu Val Met Lys Gly Glu Asp Leu Gly Ser Gln Phe Leu Asp Ile Ala    339
GAG GTG ATG AAA GGG GAA GAC CTT GGA AGC CAG TTC CTT GAC ATA GCG    1056

Gly Leu Lys Ile Pro Val Glu Glu Met Lys Gly Asn Met Leu Val Phe    355
GGG CTA AAA ATC CCG GTT GAG GAG ATG AAG GGT AAC ATG CTG GTC TTC    1104

Val Pro Thr Arg Asn Met Ala Val Asp Val Ala Lys Lys Leu Lys Ala    371
GTA CCC ACA AGA AAC ATG GCA GTT GAT GTA GCC AAG AAA CTA AAA GCC    1152

Lys Gly Tyr Asn Ser Gly Tyr Tyr Tyr Ser Gly Glu Asp Pro Ala Asn    387
AAG GGC TAC AAC TCA GGG TAT TAC TAC AGT GGG GAA GAC CCG GCT AAC    1200

Leu Arg Val Val Thr Ser Gln Ser Pro Tyr Val Val Val Ala Thr Asn    403
TTG AGG GTG GTA ACA TCA CAG TCC CCA TAC GTC GTA GTA GCC ACC AAT    1248

Ala Ile Glu Ser Gly Val Thr Leu Pro Asp Leu Asp Thr Val Val Asp    419
GCC ATT GAG TCA GGG GTA ACG CTG CCA GAT TTA GAT ACA GTT GTT GAC    1296

Thr Gly Leu Lys Cys Glu Lys Arg Val Arg Val Ser Ser Lys Ile Pro    435
ACA GGT CGT AAG TGT GAA AAG AGG GTG AGG GTG TCA TCA AAA ATA CCT    1344

Phe Ile Val Thr Gly Leu Lys Arg Met Ala Val Thr Val Gly Glu Gln    451
TTC ATA GTA ACA GGC CTT AAA AGA ATG GCT GTC ACT GTG GGC GAA CAG    1392

Ala Gln Arg Arg Gly Arg Val Gly Arg Val Lys Pro Gly Arg Tyr Tyr    467
GCT CAG CGA AGA GGC AGG GTA GGT AGA GTG AAG CCC GGT AGG TAC TAT    1440

Arg Ser Gln Glu Thr Ala Thr Gly Ser Lys Asp Tyr His Tyr Asp Leu    483
AGA AGC CAG GAA ACA GCG ACC GGG TCA AAG GAC TAC CAC TAT GAC CTG    1488

Leu Gln Ala His Arg Tyr Gly Ile Glu Asp Gly Ile Asn Val Thr Lys    499
TTA CAG GCA CAC AGG TAT GGG ATA GAA GAT GGA ATC AAC GTG ACA AAG    1536

Ser Phe Arg Glu Met Asn Tyr Asp Trp Ser Leu Tyr Glu Glu Asp Ser    515
TCC TTT AGG GAA ATG AAT TAC GAT TGG AGC CTG TAC GAG GAC GAC AGC    1584

Leu Leu Ile Thr Gln Leu Glu Ile Leu Asn Asn Leu Leu Ile Ser Glu    531
TTG CTG ATA ACG CAG CTG GAG ATA CTG AAC AAT CTA CTC ATC TCT GAA    1632

Asp Leu Pro Ala Ala Val Lys Asn Ile Met Ala Arg Thr Asp His Pro    547
GAC CTA CCA GCA GCA GTA AAA AAC ATC ATG GCA AGG ACT GAT CAC CCA    1680
```

-continued
LIST OF SEQUENCES.

Glu Pro Ile Gln Leu Ala Tyr Asn Ser Tyr Glu Val Gln Val Pro Val 563
GAA CCA ATC CAG CTT GCA TAC AAC AGT TAT GAG GTC CAG GTC CCT GTA 1728

Leu Phe Pro Lys Ile Arg Asn Gly Glu Val Thr Asp Thr Tyr Glu Asn 579
CTG TTT CCA AAA ATA AGG AAT GGG GAG GTT ACA GAT ACT TAC GAG AAC 1776

Tyr Ser Phe Leu Asn Ala Arg Lys Leu Gly Glu Asp Val Pro Val Tyr 595
TAC TCA TTC CTA AAT GCA AGA AAA CTA GGG GAA GAT GTA CCT GTG TAC 1824

Ile Tyr Ala Thr Glu Asp Glu Asp Leu Ala Val Asp Leu Leu Glu Leu 611
ATT TAT GCC ACC GAA GAT GAA GAC CTG GCA GTA GAC CTT CTA GGC TTG 1872

Asp Trp Pro Asp Pro Gly Asn Gln Gln Val Val Glu Thr Gly Lys Ala 627
GAC TGG CCC GAC CCA GGG AAC CAG CAA GTA GTG GAG ACT GGG AAA GCA 1920

Leu Lys Gln Val Val Gly Leu Ser Ser Ala Glu Asn Ala Leu Leu Ile 643
CTG AAG CCA GTG GTA GGA CTG TCC TCT GCT GAG AAT GCC CTG CTA ATA 1968

Ala Leu Phe Gly Tyr Val Gly Tyr Gln Ala Leu Ser Lys Arg His Val 659
GCC CTG TTT GGG TAT GTA GGA TAT CAA GCT TTG TCA AAA AGA CAC GTC 2016

Pro Met Ile Thr Asp Ile Tyr Thr Ile Glu Asp Gln Arg Leu Glu Asp 675
CCA ATG ATC ACA GAC ATA TAC ACC ATA GAA GAT CAA AGA CTA GAG GAC 2064

Thr Thr His Leu Gln Tyr Ala Pro Asn Ala Ile Arg Thr Glu Gly Lys 691
ACA ACC CAC CTC CAA TAT GCA CCT AAT GCT ATA AGA ACT GAG GGG AAG 2112

Glu Thr Glu Leu Lys Glu Leu Ala Val Gly Asp Met Asp Arg Ile Met 707
GAG ACT GAA CTA AAG GAA TTA GCA GTG GGT GAC ATG GAC AGA ATC ATG 2160

Glu Ser Ile Ser Asp Tyr Ala Ser Gly Gly Leu Thr Phe Ile Arg Ser 723
GAA TCC ATC TCA GAT TAT GCA TCA GGA GGG TTG ACA TTC ATA AGA TCT 2208

STOP
Gln Ala Glu Lys Val Arg *** 729
CAG GCA GAG AAA GTA CGC TAG CGG ATC C 2236
Bam HI

SEQ ID No: 2

TYPE OF SEQUENCE: nucleotide sequence
LENGTH OF SEQUENCE: 240 base pairs
NUMBER OF STRANDS: single
CONFIGURATION: linear
TYPE OF MOLECULE: cDNA for genomic RNA
ORIGIN: BVD Osloss
REGION TRANSLATED: 1–240
PROPERTIES: encodes a p80 region 80 amino acids comprising epitopes recognised by anti-p80 monoclonal antibodies.

Gly Tyr Gln Ala Leu Ser Lys Arg His Val Pro Met Ile Thr Asp Ile 16
GGA TAT CAA GCT TTG TCA AAA AGA CAC GTC CCA ATG ATC ACA GAC ATA 48

Tyr Thr Ile Glu Asp Gln Arg Leu Glu Asp Thr Thr His Leu Gln Tyr 32
TAC ACC ATA GAA GAT CAA AGA CTA GAG GAC ACA ACC CAC CTC CAA TAT 96

Ala Pro Asn Ala Ile Arg Thr Glu Gly Lys Glu Thr Glu Leu Lys Glu 48
GCA CCT AAT GCT ATA AGA ACT GAG GGG AAG GAG ACT GAA GTA AAG GAA 144

Leu Ala Val Gly Asp Met Asp Arg Ile Met Glu Ser Ile Ser Asp Tyr 64
TTA GCA GTG GGT GAC ATG GAC AGA ATC ATG GAA TCC ATC TCA GAT TAT 192

Ala Ser Gly Gly Leu Thr Phe Ile Arg Ser Gln Ala Glu Lys Val Arg 80
GCA TCA GGA GGG TTG ACA TTC ATA AGA TCT CAG GCA GAG AAA GTA AGA 240

We claim:

1. A method for detecting infection of a blood sample by a bovine diarrhoea virus (BVD), comprising a first test for the detection of anti-bovine diarrhoea virus antibodies and a second test for the detection of viral particles wherein anti-p80 antibodies are detected by means of a recombinant p80 antigen encoded by SEQ ID NO:1 produced in a eukaryotic host, and wherein the presence of viral particles i detected by means of antibodies directed against bovine diarrhoea virus protein p80, for the recognition of any bovine diarrhoea virus strain maintaining BDV antigenic recognition and detection of persistent viremias and acute infections caused by any bovine diarrhoea virus strain.

2. A method according to claim 1 wherein the recombinant p80 antigen is obtained from animal cell cultures transfected with a suitable vector expressing the p80 protein.

3. A method according to claim 2 wherein the recombinant p80 antigen is obtained from cultures of insect cells.

4. A method according to claim 2 wherein the recombinant p80 antigen is obtained from cultures of mammalian cells.

5. A method according to claim 1 wherein the recombinant p80 antigen is obtained from cultures of yeast cells transfected with a suitable vector expressing the p80 protein.

6. A method according to claim 1 wherein the recombinant p80 antigen comprises extracts of eukaryotic host cells transfected with a suitable vector expressing the p80 protein.

7. A method according to claim 1 wherein the p80 protein is obtained by expression in a viral or eukaryotic vector.

8. A method according to claim 7 wherein the p80 protein is expressed in the Baculovirus system.

9. A method according to claim 1 wherein the anti-p80 antibodies are detected in any blood fraction.

10. A method according to claim 1 wherein the recombinant p80 antigen is immobilized on a solid support.

11. A method according to claim 1 wherein the presence of anti-p80 antibodies is revealed by a bovine anti-IgG antiserum coupled to a stain.

12. A method according to claim 1 wherein the presence of antibodies is revealed by a competition ELISA, in the presence of an anti-p80 monoclonal antibody coupled to a stain.

13. A method according to claim 1 wherein the presence of viral particles in crude or white blood cell-enriched whole blood is detected by centrifugation.

14. A method according to claim 1 wherein the presence of viral particles is detected by means of a serum directed against the recombinant p80 antigen produced in a eukaryotic or prokaryotic host.

15. A method according to claim 1 wherein a mixture of three viral p80-specific monoclonal antibodies is used for the detection of viral particles.

16. A method according to claim 15 wherein a sandwich type ELISA is carried out using a mixture of three viral p80-specific monoclonal antibodies as captor and the serum as stain.

17. A method according to claim 1 wherein the recombinant antigen is immobilized on a support via an anti-p80 monoclonal antibody.

18. A method according to claim 3 wherein the recombinant p80 antigen is obtained from cultures of *Spodoptera frugiperda* cells.

19. A method according to claim 4 wherein the recombinant p80 antigen is obtained from cultures of mammalian cells selected from the group consisting of HeLa, CHO and BHK cells.

20. A method according to claim 5 wherein the yeast cells are from *Saccharomyces cerevisiae*.

21. A method according to claim 8 wherein the Baculovirus system is Baculovirus AcNPV.

22. A method according to claim 9 wherein the bovine blood fraction is serum or plasma.

* * * * *